United States Patent
Levy et al.

(10) Patent No.: US 11,857,807 B2
(45) Date of Patent: Jan. 2, 2024

(54) SIMULATION-BASED DRUG TREATMENT PLANNING

(71) Applicants: Yoav Levy, Hinanit (IL); Rafi De Picciotto, Tirat Carmel (IL); Javier Grinfeld, Tel Aviv-Jaffa (IL); Eyal Zadicario, Tel Aviv-Jaffa (IL)

(72) Inventors: Yoav Levy, Hinanit (IL); Rafi De Picciotto, Tirat Carmel (IL); Javier Grinfeld, Tel Aviv-Jaffa (IL); Eyal Zadicario, Tel Aviv-Jaffa (IL)

(73) Assignee: INSIGHTEC, LTD., Tirat Carmel (IL)

( * ) Notice: Subject to any disclaimer, the term of this patent is extended or adjusted under 35 U.S.C. 154(b) by 913 days.

(21) Appl. No.: 16/622,050

(22) PCT Filed: Jun. 29, 2018

(86) PCT No.: PCT/IB2018/000834
§ 371 (c)(1),
(2) Date: Dec. 12, 2019

(87) PCT Pub. No.: WO2019/002943
PCT Pub. Date: Jan. 3, 2019

(65) Prior Publication Data
US 2020/0171327 A1 Jun. 4, 2020

Related U.S. Application Data

(63) Continuation-in-part of application No. 15/637,163, filed on Jun. 29, 2017, now Pat. No. 11,123,575.
(Continued)

(51) Int. Cl.
*A61M 37/00* (2006.01)
*A61N 7/00* (2006.01)
(Continued)

(52) U.S. Cl.
CPC ............ *A61N 5/1049* (2013.01); *A61B 5/489* (2013.01); *A61B 34/10* (2016.02);
(Continued)

(58) Field of Classification Search
CPC ...................... A61M 37/0092; A61B 2034/104
See application file for complete search history.

(56) References Cited

U.S. PATENT DOCUMENTS

| | | |
|---|---|---|
| 2004/0122323 A1 | 6/2004 | Vortman et al. |
| 2007/0016039 A1 | 1/2007 | Vortman et al. |

(Continued)

FOREIGN PATENT DOCUMENTS

| | | |
|---|---|---|
| CN | 105682739 A | 6/2016 |
| EP | 2343103 A1 | 7/2011 |

(Continued)

OTHER PUBLICATIONS

International Search Report and Written Opinion of the International Searching Authority dated Nov. 19, 2018 for International Application No. PCT/IB18/000841 (11 pages).
(Continued)

*Primary Examiner* — Amelie R Davis
(74) *Attorney, Agent, or Firm* — Morgan, Lewis & Bockius LLP (57) ABSTRACT

Various approaches for computationally generating a protocol for treatment of one or more target BBB regions within a tissue region of interest using a source of focused ultrasound include specifying (i) settings of sonication parameters for applying one or more sequence of sonications to the target BBB region using the source of focused ultrasound and (ii) a characteristic of microbubbles selected to be administered into the target BBB region; electronically simulating treatment in accordance with the protocol at least in part by computationally executing the sequence(s) of
(Continued)

sonications and computationally administering the microbubbles having the characteristic; and computationally predicting a tissue disruption effect of the target BBB region resulting from the treatment.

20 Claims, 4 Drawing Sheets

Related U.S. Application Data (60) Provisional application No. 62/597,076, filed on Dec. 11, 2017, provisional application No. 62/597,073, filed on Dec. 11, 2017, provisional application No. 62/526,550, filed on Jun. 29, 2017, provisional application No. 62/526,545, filed on Jun. 29, 2017, provisional application No. 62/526,548, filed on Jun. 29, 2017.

(51) Int. Cl.
*A61N 5/10* (2006.01)
*A61B 5/00* (2006.01)
*A61N 7/02* (2006.01)
*A61B 34/10* (2016.01)
*A61B 6/12* (2006.01)
*A61B 6/03* (2006.01)
*A61B 6/00* (2006.01)

(52) U.S. Cl.
CPC ......... *A61M 37/0092* (2013.01); *A61N 5/103* (2013.01); *A61N 5/1039* (2013.01); *A61N 5/1048* (2013.01); *A61N 5/1064* (2013.01); *A61N 7/02* (2013.01); *A61B 5/4836* (2013.01); *A61B 6/03* (2013.01); *A61B 6/12* (2013.01); *A61B 6/504* (2013.01); *A61N 2005/1052* (2013.01); *A61N 2005/1055* (2013.01); *A61N 2005/1058* (2013.01); *A61N 2005/1061* (2013.01); *A61N 2005/1087* (2013.01); *A61N 2005/1092* (2013.01); *A61N 2005/1098* (2013.01); *A61N 2007/0004* (2013.01); *A61N 2007/0039* (2013.01); *A61N 2007/0052* (2013.01); *A61N 2007/0082* (2013.01); *A61N 2007/027* (2013.01)

(56) References Cited

U.S. PATENT DOCUMENTS

| | | | |
|---|---|---|---|
| 2008/0030104 A1* | 2/2008 | Prus | B06B 1/0622 310/334 |
| 2008/0221382 A1 | 9/2008 | Karshafian et al. | |
| 2010/0143241 A1 | 6/2010 | Johnson et al. | |
| 2010/0179425 A1 | 7/2010 | Zadicario | |
| 2012/0116221 A1 | 5/2012 | Sehgal et al. | |
| 2013/0046229 A1 | 2/2013 | Konofagou et al. | |
| 2013/0331738 A1 | 12/2013 | Borelli | |
| 2014/0343421 A1 | 11/2014 | Kim et al. | |
| 2014/0378737 A1 | 12/2014 | Carpenter et al. | |
| 2015/0196638 A1 | 7/2015 | Czarnota et al. | |
| 2015/0359603 A1* | 12/2015 | Levy | A61N 7/02 703/2 |
| 2018/0071553 A1 | 3/2018 | Vortman et al. | |
| 2019/0083065 A1 | 3/2019 | Vitek et al. | |
| 2019/0178851 A1 | 6/2019 | Prus et al. | |
| 2019/0350486 A1 | 11/2019 | Walczak et al. | |
| 2020/0085409 A1 | 3/2020 | Grinfeld et al. | |
| 2020/0323515 A1 | 10/2020 | Levy | |
| 2021/0187331 A1 | 6/2021 | Zadicario et al. | |

FOREIGN PATENT DOCUMENTS

| | | |
|---|---|---|
| EP | 2676702 A1 | 12/2013 |
| WO | WO2010118307 A1 | 10/2010 |
| WO | WO2013034709 A1 | 3/2013 |
| WO | WO2014/053950 A1 | 4/2014 |
| WO | 2014118632 A1 | 8/2014 |
| WO | WO2018/020315 A1 | 2/2018 |
| WO | WO2018/130867 A1 | 7/2018 |
| WO | WO2019/002947 A1 | 1/2019 |
| WO | WO2019/058171 A1 | 3/2019 |
| WO | WO2019/116095 A1 | 6/2019 |
| WO | WO2019/116097 A1 | 6/2019 |
| WO | WO2019/116107 A1 | 6/2019 |
| WO | WO2021/014221 A1 | 1/2021 |

OTHER PUBLICATIONS

International Search Report and Written Opinion of the International Searching Authority dated Nov. 28, 2018 for International Application No. PCT/IB18/000811 (12 pages).
Extended European Search Report, EP18180302.4, dated Nov. 21, 2018, 5 pgs.
Decision to Grant, EP18180302.4, dated Jan. 30, 2020, 2 pgs.
Decision to Grant, EP18768933.6, dated Jul. 1, 2021, 3 pgs.
Insightec, Ltd., Allowance Notification for Invention, CN201880043567.3, dated Jan. 30, 2022, 2 pgs.
Vlacos, F. et al., "Permeability Assessment of the Focused Ultrasound-Induced Blood-Brain Barrier Opening Using Dynamic Contrast-Enhanced MRI," Phys. Med. Biol. 55 (2010) 5451-5466, 16 pages.
Vortman, Office Action, U.S. Appl. No. 15/637,163, May 13, 2019, 15 pgs.
Vortman, Office Action, U.S. Appl. No. 15/637,163, dated Dec. 6, 2019, 12 pgs.
Vortman, Office Action, U.S. Appl. No. 15/637,163, dated May 21, 2020, 14 pgs.
Vortman, Final Office Action, U.S. Appl. No. 15/637,163, dated Sep. 18, 2020, 14 pgs.
Vortman, Notice of Allowance, U.S. Appl. No. 15/637,163, dated May 28, 2021, 11 pgs.
International Search Report and Written Opinion of the International Searching Authority dated Nov. 12, 2018 for International Application No. PCT/IB18/00834 (13 pages).
Insightec, Ltd., International Search Report and Written Opinion of the International Searching Authority dated Nov. 23, 2020 for International Application No. PCT/IB2020/000677 (17 pages).
Insightec, Ltd., Communication Pursuant to Article 94(3), EP18759374.4, Sep. 20, 2021, 4 pgs.
First Office Action, CN201880056389, dated Feb. 1, 2021, 19 pgs.
Second Office Action, CN201880056389, dated Aug. 30, 2021, 19 pgs.
First Office Action, CN201880043399.8, dated Feb. 2, 2021, 7 pgs.
Notification to Grant Patent Right for Invention, CN201880043399-8, dated Aug. 30, 2021, 3 pgs.
De Picciotto, Notice of Allowance, U.S. Appl. No. 16/622,004, dated May 5, 2022, 9 pgs.
Levy, Office Action, U.S. Appl. No. 16/622,005, dated Sep. 28, 2022, 21 pgs.
Jolesz FA. MRI-guided focused ultrasound surgery. Annu Rev Med. 2009;60:417-30. doi: 10.1146/annurev.med.60.041707.170303. PMID: 19630579; PMCID: PMC4005559 (Year: 2009), 17 pgs.
Park et al., Evaluation of permeability, doxorubicin delivery, and drug retention in a rat brain tumor model after ultrasound-induced blood-tumor barrier disruption, Journal of Controlled Release, vol. 250, Mar. 28, 2017, pp. 77-85 (Year: 2017), 9 pgs.
Chai et al., Magnetic-resonance imaging for kinetic analysis of permeability changes during focused ultrasound-induced blood-brain barrier opening and brain drug delivery, Journal of Controlled Release, vol. 192, Oct. 28, 2014, pp. 1-9 (Year: 2014), 9 pgs.

\* cited by examiner

SIMULATION-BASED DRUG TREATMENT PLANNING

CROSS-REFERENCE TO RELATED APPLICATION

This application is a U.S. National Phase Application of PCT/M2018/000834, filed Jun. 29, 2018, which claims priority to, and the benefit of, U.S. Patent Application Nos. 62/526,548 (filed on Jun. 29, 2017), 62/526,545 (filed on Jun. 29, 2017), 62/526,550 (filed on Jun. 29, 2017), Ser. No. 15/637,163 (filed on Jun. 29, 2017), 62/597,073 (filed on Dec. 11, 2017), and 62/597,076 (filed on Dec. 11, 2017). The entire disclosures of these priority documents are hereby incorporated by reference.

FIELD OF THE INVENTION

The invention relates generally to drug treatment planning. More specifically, various embodiments are directed to computing systems and methods for simulating and adjusting a cavitation-enhanced drug-treatment procedure prior to execution.

BACKGROUND

The blood-brain barrier (BBB), formed by layers of cells in the central nervous system (CNS), excludes large molecules from the brain parenchyma, thereby protecting it from damage by toxic foreign substances. But the BBB also presents one of the largest obstacles to treating many brain diseases. Specifically, the BBB prevents many therapeutic agents, such as drugs and gene-therapy vectors, from reaching a patient's brain tissue. For example, treatments for CNS infections, neurodegenerative diseases, congenital enzyme defects and brain cancer are all hampered by the ability of the BBB to block passage of agents such as antibiotics, anti-retroviral drugs, enzyme replacements, gene preparations and anti-neoplastic drugs. It is thus desirable to temporarily and locally "open" the BBB to permit therapeutic quantities of these agents to reach the affected brain tissue.

Focused ultrasound (i.e., acoustic waves having a frequency greater than about 20 kiloHertz) has been utilized to open the BBB in the treatment of neurological diseases. The mechanistic event underlying this effect appears to involve the reaction of microbubbles to ultrasonic pulses, which can result in an array of behaviors known as acoustic cavitation. In stable cavitation, microbubbles expand and contract with the acoustic pressure rarefaction and compression over several cycles; such action can result in dilation and contraction of blood vessels in the vicinity. In inertial cavitation, the microbubbles can expand to several factors greater than their equilibrium radius and subsequently collapse due to the inertia of the surrounding tissue. In both cases, the consequent disruption of blood vessels induces "opening" of the BBB.

Typically, microbubbles are introduced by systemic injection, either into the patient's brain or locally into the target BBB region(s). The number of injections and volume of injected microbubbles in a treatment is limited. This presents challenges to microbubble-induced BBB opening, in particular, when the target tumor tissue spans a relatively large area that requires more than one region of the BBB to be opened and/or when multiple target tumors are identified for treatment.

In addition, an uncontrolled microbubble cavitation event may result in undesired damage to and around the BBB. For example, ablating cells forming portions of the BBB may not only compromise BBB function but also cause unwanted cell death or necrosis in surrounding tissue. To minimize the undesired effects of microbubble cavitation during BBB disruption, one conventional approach utilizes a passive cavitation detector that measures the acoustic response of the microbubbles after each ultrasound sonication. The BBB disruption effects, however, may result from other microbubble characteristics (e.g., size, concentration, or administration profile). For example, the magnitude and number of BBB openings may correlate with the microbubble sizes and/or concentrations. Further, acoustic properties (e.g., the spatial power distribution, the temporal power distribution or the shape of the focal zone) of the ultrasound pulses applied to the microbubbles may affect BBB opening properties (e.g., magnitude or number). As a result, BBB opening procedures that utilize microbubbles may reach a level of complexity that requires detailed advance planning in order to achieve desired objectives.

SUMMARY

Embodiments of the present invention are directed to systems and methods of treatment planning that involve simulating the planned procedure computationally and, typically, adjusting the procedure iteratively based on the simulation. The treatment may broadly involve targeted drug delivery, radiation therapy or any other applicable therapeutic method. In various embodiments, the treatment is enhanced by ultrasound-induced microbubble cavitation. As a result, the treatment procedure generally involves multiple steps, such as (i) administration of microbubbles into the patient's bloodstream, (ii) sonicating the microbubbles to cause microbubble cavitation and thereby open the BBB, and (iii) administration of a therapeutic agent to treat the target region via the BBB opening or activation of a radiation device to emit an ionizing beam to treat the target region.

The simulations described herein generally include modeling one or more tissue regions of interest and one or more microbubble characteristics at the tissue region(s), computationally modeling the effect of sonicating the microbubbles, and based thereon, computationally predicting the effects of the microbubbles on the tissue region(s), typically as a function of time. In various embodiments, the tissue region is represented as a set of voxels (i.e., volumetric pixels) based on a three-dimensional (3D) image or a series of two-dimensional (2D) image slices and may include the target tumor region, the target BBB region in the vicinity of the target tumor for disruption, and, typically, non-target tissues—e.g., tissues surrounding the target tumor and target BBB regions and/or tissues located between an ultrasound transducer and the target tumor/BBB. The tissue region may dynamically move over time (e.g., during the respiratory cycle); accordingly, in another embodiment, the tissue region is modeled as a four-dimensional (4D) representation—i.e., 3D set of voxels and a time dimension. As a result, the treatment plan occurs in 4D and adjusts various treatment profile parameters (e.g., sonication properties and/or the microbubble characteristics) for treating a volumetric region as a function of time. The simulation typically utilizes two types of information: tissue information (e.g., the target location and the nature and extent of intervening tissue) acquired prior to the simulation using, for example, an imaging device, and known relationships among applied acoustic power or energy, microbubble cavitation and the resulting tissue disruption of a target BBB region.

In various embodiments, microbubble characteristics are modeled based on the agent type(s), sizes, concentrations, administration profiles (e.g., a dose or timing), and/or locations of the injection site relative to the bloodstream and the target BBB region. In general, the simulation includes a physical model specifying the geometry as well as the position and orientation of the ultrasound transducer relative to the microbubbles at the target BBB region. The sonications may include, e.g., a series of pulses directed toward the target BBB region along a desired focus path. Predicting the effect of the microbubbles generally includes modeling the cavitation events induced by the sonications and tissue disruption effects resulting from cavitation at the target BBB region. By "tissue disruption effect" is meant a change in the permeability, structure, size, shape, and/or blood flow rate in the tissue; and/or the vascular physiology or morphology, or other physiology or morphology of the tissue, particularly as it affects the ability of drugs to penetrate the tissue and/or the radiation dose to efficiently treat the target tumor.

Cavitation events may be simulated as an acoustic response level corresponding to the expected temporal acoustic response of the microbubbles to each sonication pulse and/or as an acoustic response dose that estimates the response of the microbubbles to the acoustic energy accumulated over a single sonication or multiple sonications. In addition, the disruption effects experienced by the target BBB region may be simulated based on the amount of microbubble cavitation, the microbubble concentration, and/or the delivered acoustic power (or power density) and energy in the tissue region(s) in accordance with a physical model. In various embodiments, the tissue-disruption effects are captured with a suitable biological parameter (e.g., a perfusion rate or tissue permeability). For example, the BBB regions that have been opened by the microbubble cavitation may have a higher perfusion rate and/or tissue permeability than the BBB regions that have not been disrupted.

In various embodiments, tissue disruption in multiple BBB regions is simulated. For example, the target tumor region may span a large volume such that disruption of multiple BBB regions is necessary for efficient treatment. Alternatively, multiple target tumor regions may be identified for treatment, each requiring a corresponding BBB region to be opened. Accordingly, treatment planning may computationally simulate treatments that are sequentially or substantially simultaneously performed on different target BBB regions, preferably taking the treatment effect in one region into account when simulating another region. For example, two target BBB regions may be located in the bloodstream, one upstream of the other; disruption of the upstream target BBB region utilizing microbubble cavitation may reduce the concentration of microbubbles available to the downstream target BBB region, thereby reducing the extent of disruption. Such effects may be predicted based on previously acquired image information (such as the locations of the two BBB target regions and their locations in the bloodstream) and/or a physical model. Additionally or alternatively, imaging information may be collected in an exploratory phase prior to treatment, where microbubbles are administered but destroyed in one target BBB region and the effect on another target BBB region(s) may be tracked by imaging or detection of the acoustic response therefrom after application of another series of sonications thereto.

In various embodiments, the computed cavitation event and/or tissue disruption effects of a simulated treatment procedure are compared against desired target objectives, including, e.g., a target amount of cavitation, a target degree and/or a target size of tissue disruption (characterized by, for example, a target perfusion rate or a target tissue permeability) at the target BBB region, and/or a safety threshold associated with a non-target region. If the computational prediction deviates from the desired target objectives, the simulated treatment procedure is adjusted. The adjustment may take one of two forms: the treatment plan can either be "rolled back"—reverting to previous settings of the treatment profile parameters (e.g., microbubble characteristics and/or delivered acoustic power)—or extended to include further sonications. For example, if the simulation does not generate tissue disruption throughout the target BBB region, this can be remedied by increasing the microbubble concentration/dosage at the target BBB region, increasing the energy or intensity of the planned sonications in the target BBB region, and/or by adding more sonications at the target BBB region. Conversely, if the computed tissue disruption in a non-target region exceeds the safety threshold, suitable modifications to the treatment plan may include a reduction in the energy or intensity of sonications applied to the target BBB region and/or a reduction of the planned microbubble concentration/dosage. The treatment plan may be simulated and adjusted iteratively until the simulated tissue disruption effect no longer deviates by more than a tolerable amount (e.g., 10%) from the desired target objectives.

Treatment may be carried out in accordance with the completed treatment plan. For example, an ultrasound transducer may be operated based on the sonication parameter values (e.g., amplitudes, frequencies, phases, directions, or time intervals between consecutive series of sonications) determined in the simulation. As a simplified example, the simulation may be run in order to optimize a time interval between consecutive sequences of sonications, thereby allowing the microbubbles to be replenished at the target BBB region prior to the next sonication sequence; the optimized time interval is utilized during treatment. In some embodiments, the treatment effect on the target BBB region (e.g., the degree and/or size of tissue disruption) is monitored during treatment (e.g., by using the imaging device or any suitable approach). If discrepancies between the monitored treatment effect and the previously computed treatment effect are discovered, the treatment plan may be modified. Discrepancies may arise, for example, from inaccuracies in certain parameters of the physical model underlying the simulation. Accordingly, in various embodiments, the measurements taken during actual treatment are used as feedback to adjust the parameters. A new treatment plan may then be generated (or treatment altered in real time) using the adjusted parameters. Alternatively, in various circumstances, a straightforward adjustment of the existing treatment plan may be carried out, e.g., by propagating the adjustment of the parameter(s) through the model.

Accordingly, in one aspect, the invention pertains to a method of computationally generating a protocol for treatment of one or more target BBB regions within a tissue region of interest using a source of focused ultrasound. In various embodiments, the method includes (a) specifying (i) a setting of one or more sonication parameters (e.g., an amplitude, a frequency, a beam shape, a phase and/or a direction of the sonication in the sequence) for applying one or more sequences of sonications to the target BBB region using the source of focused ultrasound and (ii) a characteristic (e.g., an agent type, a size, a concentration, a dose, an administration rate or timing, and/or a location of an injection site) of microbubbles selected to be administered into the target BBB region; (b) electronically simulating treatment in accordance with the specified sonication parameter setting and microbubble characteristic at least in part by computationally executing the sequence(s) of sonications and computationally administering the microbubbles having the characteristic; (c) computationally predicting a degree of tissue disruption of the target BBB region resulting from the treatment based on the simulation thereof; and (d) generating the protocol based at least in part on the predicted degree of tissue disruption. As used herein, by "degree of tissue disruption" is meant any quantitative or qualitative measure of a change in the permeability properties of the target BBB region. For example, tissue disruption can be measured in terms of the size of molecules that can penetrate the target BBB, their rate of transmission through the target BBB, etc.

The degree of tissue disruption may be predicted as a function of time. In one embodiment, the method further includes (e) comparing the predicted degree of tissue disruption against a target objective (e.g., opening of the target BBB region, a target perfusion rate at the target BBB region, a target tissue permeability at the target BBB region, a safety threshold associated with target BBB region and/or a safety threshold associated with tissue outside the target BBB region); and (f) if the predicted degree of tissue disruption deviates from the target objective, altering the treatment protocol and repeating steps (b) through (e) for the altered treatment protocol. In another embodiment, the treatment protocol specifies multiple sequences of sonications; the method further includes (e) comparing the predicted degree of tissue disruption against the target objective; and (f) if the predicted degree of tissue disruption deviates from the target objective, altering (i) the sonication parameter in a subsequent sequence of sonications and/or (ii) the microbubble characteristic, and repeating steps (b) through (e).

The treatment protocol may specify multiple sequences of sonications and the sonication parameter is a time interval between consecutive sonication sequences. In addition, the method may include obtaining a digital image of at least a portion of the target BBB region and computationally identifying a set of 3D voxels corresponding to the portion of the target BBB region; the treatment protocol is then created based on the identified 3D voxels. In various embodiments, multiple target BBB regions are identified in the image and the treatment protocol specifies multiple sonication sequences, each corresponding to one of the target BBB regions. The multiple sonication sequences may be applied to the target BBB regions substantially simultaneously. Alternatively, the sonication sequences may be sequentially applied to the target BBB regions in round-robin fashion. In some embodiments, the method further includes computationally predicting microbubble cavitation resulting from the computationally executed sonications; the degree of tissue disruption of the target BBB region is then predicted based at least in part on the predicted microbubble cavitation. In addition, the setting of the sonication parameter associated with the second sonication sequence applied to the second target BBB region may be determined based at least in part on the predicted microbubble cavitation and/or the degree of tissue disruption resulting from the first sonication sequence previously applied to the first target BBB region. When multiple tissue types are identified in the target BBB region of the image; the treatment protocol may specify multiple sonication sequences, each corresponding to one tissue type of the target BBB region.

In various embodiments, the degree of tissue disruption is predicted by computationally simulating administration of an MRI contrast agent into the target BBB region and diffusion thereof. In addition, the method may further include (e) using an ultrasound transducer to transmit one or more sequence of sonications in accordance with the setting in the treatment protocol; (f) experimentally monitoring a treatment effect resulting from the sonications; (g) comparing the experimentally monitored treatment effect with the computationally predicted degree of tissue disruption; and (h) upon detection of a discrepancy between the experimentally monitored treatment effect and the predicted degree of tissue disruption, adjusting the sonication parameter and/or the microbubble characteristic in the treatment protocol. The method may further include computationally administering a therapeutic agent into the target BBB region and computationally predicting a treatment effect of the tissue region resulting from the therapeutic agent. In one embodiment, the method further includes computationally applying a radiation dose to the tissue region and computationally predicting a treatment effect thereof resulting from the radiation dose.

In another aspect, the invention relates to a system for computationally generating a protocol for treatment of one or more target BBB regions within a tissue region of interest using a source of focused ultrasound. In various embodiments, the system includes a processor; and memory storing the treatment protocol specifying (i) a setting of one or more sonication parameters (e.g., an amplitude, a frequency, a beam shape, a phase and/or a direction of the sonication in the sequence) for applying one or more sequences of sonications to the target BBB region using the source of focused ultrasound, (ii) a characteristic (e.g., an agent type, a size, a concentration, a dose, an administration rate or timing, and/or a location of an injection site) of microbubbles selected to be administered into the target BBB region, and (iii) instructions which, when executed by the processor, cause the processor to (a) electronically simulate treatment in accordance with the specified sonication parameter setting and microbubble characteristic at least in part by computationally executing the sequence(s) of sonications and computationally administer the microbubbles having the characteristic; (b) computationally predict a degree of tissue disruption of the target BBB region resulting from the treatment based on the simulation thereof; and (c) computationally generate the protocol based at least in part on the predicted degree of tissue disruption.

The processor may be further configured to predict the degree of tissue disruption as a function of time. In one embodiment, the processor is further configured to (d) compare the predicted degree of tissue disruption against a target objective (e.g., opening of the target BBB region, a target perfusion rate at the target BBB region, a target tissue permeability at the target BBB region, a safety threshold associated with target BBB region and/or a safety threshold associated with tissue outside the target BBB region); and (e) if the predicted degree of tissue disruption deviates from the target objective, alter the treatment protocol and repeat (a) through (d) for the altered treatment protocol. In another embodiment, the treatment protocol specifies multiple sequences of sonications; the processor is further configured to (d) compare the predicted degree of tissue disruption against the target objective; and (e) if the predicted degree of tissue disruption deviates from the target objective, alter (i) the sonication parameter in a subsequent sequent of sonications and/or (ii) the microbubble characteristic, and repeat (a) through (d).

The treatment protocol may specify multiple sequences of sonications and the sonication parameter is a time interval between consecutive sonication sequences. In addition, the system may include an imaging device for obtaining a digital image of at least a portion of the target BBB region; the processor is further configured to computationally identify a set of 3D voxels corresponding to the portion of the target BBB region and generate the treatment protocol based on the identified 3D voxels. In various embodiments, multiple target BBB regions are identified in the image and the treatment protocol specifies multiple sonication sequences, each corresponding to one of the target BBB regions. The processor may be further configured to substantially simultaneously apply the plurality of sonication sequences to the target BBB regions. Alternatively, the processor may be further configured to sequentially apply the plurality of sonication sequences to the target BBB regions in round-robin fashion. In some embodiments, the processor is further configured to computationally predict microbubble cavitation resulting from the computationally executed sonications, and predict the degree of tissue disruption of the target BBB region based at least in part on the predicted microbubble cavitation. In addition, the processor may be configured to determine the setting of the sonication parameter associated with the second sonication sequence applied to the second target BBB region based at least in part on (i) the predicted microbubble cavitation and/or (ii) the degree of tissue disruption resulting from the first sonication sequence previously applied to the first target BBB region. In one implementation, the processor is further configured to identify multiple tissue types in the target BBB region of the image and generate the treatment protocol specifying multiple sonication sequences, each corresponding to one of the identified tissue types.

In various embodiments, the processor is further configured to predict the degree of tissue disruption by computationally simulating administration of an MM contrast agent into the target BBB region and diffusion thereof. In addition, the system may further include a detection system; the processor is further configured to (d) cause an ultrasound transducer to transmit one or more sequences of sonications in accordance with the setting in the treatment protocol; (e) cause the detection system to monitor an actual treatment effect resulting from the sonications; (f) compare the experimentally monitored treatment effect with the computationally predicted degree of tissue disruption; and (g) upon detection of a discrepancy between the monitored treatment effect and the predicted degree of tissue disruption, adjust the sonication parameter and/or the microbubble characteristic in the treatment protocol.

The system may further include an administration system for administering a therapeutic agent into the target BBB region. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U. In one embodiment, the system further includes a radiation device for applying a radiation dose to the tissue region.

Another aspect of the invention relates to a system for disrupting target tissue including one or more target BBB regions for treatment. In various embodiments, the system includes an ultrasound transducer; an administration system for introducing microbubbles to the target BBB region; and a processor configured to (a) generate a treatment protocol at least in part by specifying (i) a setting of one or more sonication parameters (e.g., an amplitude, a frequency, a beam shape, a phase and/or a direction of the sonication in the sequence) for applying one or more sequences of sonications to the target BBB region and (ii) a characteristic (e.g., an agent type, a size, a concentration, a dose, an administration rate or timing, and/or a location of an injection site) of microbubbles selected to be administered into the target BBB region; (b) simulate treatment in accordance with the specified sonication parameter setting and microbubble characteristic at least in part by computationally executing the sequence(s) of sonications and computationally administering the microbubbles having the characteristic; (c) determining whether a simulated treatment effect of the target BBB region achieves a target objective (e.g., opening of the target BBB region, a target perfusion rate at the target BBB region, a target tissue permeability at the target BBB region, a safety threshold associated with target BBB region and/or a safety threshold associated with tissue outside the target BBB region); and (d) if so, cause the microbubbles having the characteristic to be introduced to the target BBB region and activate the ultrasound transducer in accordance with the setting of the sonication parameter.

The processor may be further configured to simulate the treatment effect as a function of time. In one embodiment, the processor is further configured to determine whether a deviation of the simulated treatment effect from the target objective exceeds a threshold; and if so, alter the setting of the sonication parameter and/or the characteristic of microbubbles in the treatment protocol and repeat (b) and (c) until the deviation is below the threshold. In another embodiment, the treatment protocol specifies multiple sequences of sonications; the processor is further configured to determine whether a deviation of the simulated treatment effect from the target objective exceeds a threshold; and if so, alter the setting of the sonication parameter in a subsequent sequence of sonications and/or the microbubble characteristic, and repeating (b) and (c).

The treatment protocol may specify multiple sequences of sonications and the sonication parameter is a time interval between consecutive sonication sequences. In addition, the system may include an imaging device for obtaining a digital image of at least a portion of the target BBB region; the processor is further configured to computationally identify a set of 3D voxels corresponding to the portion of the target BBB region and generate the treatment protocol based on the identified 3D voxels. In various embodiments, multiple target BBB regions are identified in the image and the treatment protocol specifies multiple sonication sequences, each corresponding to one of the target BBB regions. The processor may be further configured to substantially simultaneously apply the plurality of sonication sequences to the target BBB regions. Alternatively, the processor may be further configured to sequentially apply the plurality of sonication sequences to the target BBB regions in round-robin fashion. In some embodiments, the processor is further configured to computationally predict microbubble cavitation resulting from the computationally executed sonications, and simulate the treatment effect of the target BBB region based at least in part on the predicted microbubble cavitation. In addition, the processor may be further configured to determine the setting of the sonication parameter associated with the second sonication sequence applied to the second target BBB region based at least in part on (i) the predicted microbubble cavitation and/or (ii) the treatment effect resulting from the first sonication sequence previously applied to the first target BBB region. In one implementation, the processor is further configured to identify multiple tissue types in the target BBB region of the image and generate the treatment protocol specifying multiple sonication sequences, each corresponding to one of the identified tissue types.

In various embodiments, the processor is further configured to simulate the treatment effect by computationally administering an MRI contrast agent into the target BBB region to cause diffusion therein. In addition, the system may further include a detection system; the processor is further configured to (e) cause the ultrasound transducer to transmit one or more sequences of sonications in accordance with the setting in the treatment protocol; (f) cause the detection system to monitor an actual treatment effect resulting from the sonications; (g) compare the monitored treatment effect with the simulated treatment effect; and (h) upon detection of a discrepancy between the monitored treatment effect and the simulated treatment effect, adjust the sonication parameter and/or the microbubble characteristic.

In various embodiments, the administration system is further configured to introduce a therapeutic agent into the target BBB region. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/ aldoifosfamide, Bevacizumab, 5-Fluorouracil, Bleomycin, Hydroxyurea, Docetaxel, and/or Cytarabine (cytosine arabinoside, ara-C)/ara-U. In one embodiment, the system further includes a radiation device for applying a radiation dose to the tissue region.

In yet another aspect, the invention pertains to a method of disrupting target tissue including one or more target BBB regions using a source of focused ultrasound. In various embodiment, the method includes (a) generating a treatment protocol at least in part by specifying (i) a setting of one or more sonication parameters (e.g., an amplitude, a frequency, a beam shape, a phase and/or a direction of the sonication in the sequence) for applying one or more sequences of sonications to the target BBB region using the source of focused ultrasound and (ii) a characteristic (e.g., an agent type, a size, a concentration, a dose, an administration rate or timing, and/or a location of an injection site) of microbubbles selected to be administered into the target BBB region; (b) electronically simulating treatment in accordance with the specified sonication parameter setting and microbubble characteristic at least in part by computationally executing the sequence(s) of sonications, computationally administering the microbubbles having the characteristic, and computationally predicting a treatment effect at the target BBB region; (d) determining whether the predicted treatment effect at the target BBB region achieves a target objective (e.g., opening of the target BBB region, a target perfusion rate at the target BBB region, a target tissue permeability at the target BBB region, a safety threshold associated with target BBB region and/or a safety threshold associated with tissue outside the target BBB region); and (e) if so, causing the microbubbles having the characteristic to be introduced to the target BBB region and applying the sequence(s) of sonications in accordance with the sonication parameter. In one implementation, the method further includes administering a therapeutic agent into the target tissue. The therapeutic agent may include Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, and/or Cytarabine (cytosine arabinoside, ara-C)/ara-U.

As used herein, the term "substantially" means ±10% by a tissue volume, and in some embodiments, ±5% by a tissue volume. "Clinically tolerable" means having an undesired (and sometimes the lack of a desired) effect on tissue that is considered insignificant by clinicians, e.g., prior to triggering the onset of damage thereto. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Figure 1:
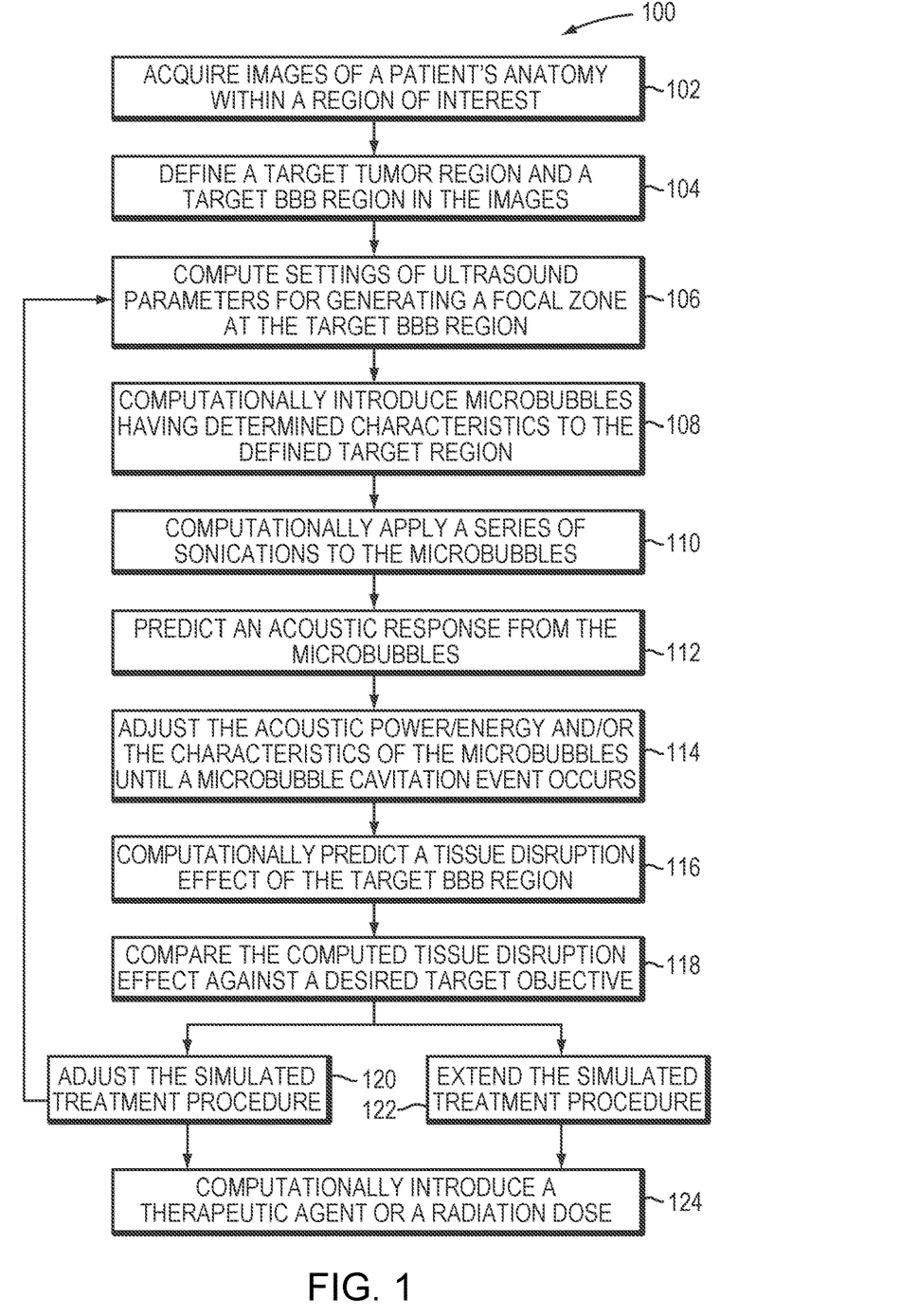
FIG. 1 is a flow chart illustrating an exemplary treatment-planning approach in accordance with various embodiments.

Various embodiments hereof provide approaches to planning treatments involving a microbubble-enhanced ultrasound procedure for targeted drug delivery, radiation therapy or any other applicable therapeutic methods within one or more tissue regions that include target tumor tissue, a target BBB region in the vicinity of the target tumor tissue, and in some embodiments, non-target tissue. Treatment planning often has the dual goals of achieving the desired treatment effect in the target tumor tissue and target BBB region (e.g., tumor ablation and BBB disruption, respectively), while at the same time avoiding damage to non-target tissue. FIG. 1 is a flow chart illustrating an exemplary treatment-planning approach 100 in accordance with various embodiments. As shown, treatment planning may begin, in step 102, with acquiring images of the patient's anatomy within a region of interest using an imaging device. The images may be 3D images or a set of 2D image slices suitable for reconstructing 3D images of the anatomic region of interest. The imaging device may be, for example, a magnetic resonance imaging (MRI) device, a computer tomography (CT) device, a positron emission tomography (PET) device, a single-photon emission computed tomography (SPECT) device, or an ultrasonography device. In step 104, a target tumor region and a target BBB region in the vicinity of the target tumor for which treatment is to be planned are identified automatically using suitable image-processing techniques or manually by a user; the target tumor and BBB regions may be defined as collections of 3D voxels. In some treatment scenarios, the target tumor consists of multiple discontiguous regions; for example, a cancer patient may be afflicted with multiple tumors or metastases that are to be treated individually. As a result, multiple BBB regions corresponding to the discontiguous tumor regions may be disrupted sequentially or substantially simultaneously. Even if the target tumor is a single, contiguous tissue region, it may span a large volume such that more than one target BBB region (disjunctive or overlapping) is necessary for effective treatment. For example, this may advantageously allow better control over ultrasound beam properties for each of the target BBB regions. In various embodiments, the target BBB region is divided in a manner that allows treatment planning for different BBB regions to be performed sequentially, possibly taking the effect of disruption of one BBB region into account when planning treatment for subsequent BBB regions, but without incurring the risk of revisiting a treatment procedure for the BBB region for which treatment planning was previously deemed complete.

Once the target BBB region is selected for treatment planning, ultrasound parameter values (e.g., amplitudes, frequencies, phases and/or directions associated with the transducer elements, or time intervals between consecutive series of sonications) are computed so that a focal zone is created at the target BBB region (in step 106). This step generally applies a physical model and takes into account the geometry as well as the position and orientation of the ultrasound transducer relative to the target BBB region. In addition, anatomic characteristics (e.g., the type, property, structure, thickness, density, etc.) and/or material characteristics (e.g., the energy absorption of the tissue at the employed frequency or the speed of sound) of the intervening tissue located on the beam path between the transducer and the target BBB region may be included in the physical model in order to predict and correct for beam aberrations resulting therefrom. In one implementation, the anatomic characteristics of the intervening tissue are acquired using the imaging device. For example, based on the acquired images of the anatomic region of interest, a tissue model characterizing the material characteristics of the target and/or non-target regions may be established. The tissue model may take the form of a 3D table of cells corresponding to the voxels representing the target and/or non-target tissue; the values of the cells represent characteristics of the tissue, such as the speed of sound, that are relevant to beam aberrations when traversing the tissue. The voxels are obtained tomographically by the imaging device and the type of tissue that each voxel represents can be determined automatically by conventional tissue-analysis software. Using the determined tissue types and a lookup table of tissue parameters (e.g., speed of sound by type of tissue), the cells of the tissue model may be populated. Further detail regarding creation of a tissue model that identifies the speed of sound, heat sensitivity and/or thermal energy tolerance of various tissues may be found in U.S. Patent Publication No. 2012/0029396, the entire disclosure of which is hereby incorporated by reference.

Accordingly, based on the anatomic and/or material characteristics of the target/non-target tissue, the physical model may predict ultrasound beam paths, ultrasound energy delivered to the target BBB region and/or non-target regions, the conversion of ultrasound energy or pressure into heat and/or tissue displacement at the target BBB region and/or non-target regions, and/or the propagation of the induced effects through the tissue. Typically, the simulation may take the form of (or include) differential equations. For example, the physical model may include the Pennes model and a bioheat equation to simulate heat transfer in tissue. Approaches to simulating the sonications and their effects on the tissue are provided, for example, in U.S. Patent Publication No. 2015/0359603, the entire disclosure of which is hereby incorporated by reference.

In an optional step 108, microbubbles having selected characteristics are computationally introduced to the defined target BBB region; the microbubble characteristics may include an agent type, a size distribution, a concentration, an administration profile (e.g., a dose and an administration timing) and/or an associated location of the site where the microbubbles are computationally administered. At a relatively low acoustic power (e.g., 1-2 Watts above the microbubble-generation threshold), the generated microbubbles tend to undergo oscillation with compression and rarefaction that are equal in magnitude and thus the microbubbles generally remain unruptured (i.e., a "stable cavitation"). At a higher acoustic power (e.g., more than 10 Watts above the microbubble-generation threshold), the microbubbles undergo rarefaction that is greater than compression, which may cause inertial (or transient) cavitation of the microbubbles in which the microbubbles in the liquid rapidly collapse. The microbubble cavitation, in turn, may result in transient disruption of the tissue in the target BBB region.

In various embodiments, the microbubble characteristics are empirically determined based on retrospective study of the patients experiencing a microbubble-enhanced ultrasound procedure. For example, the retrospective study may establish relationships between the microbubble response (e.g., a temporal acoustic effect of the microbubbles after each ultrasound sonication pulse and/or a cumulative effect of the microbubbles over a single sonication or multiple sonications) and microbubbles having various characteristics at given ultrasound settings. Microbubble characteristics having the desired microbubble response for disrupting the target BBB region may then be selected. Additionally or alternatively, the microbubble characteristics may be selected using the physical model. For example, the size distribution of the microbubbles may be selected such that a significant fraction (e.g., more than 50%, 90%, 95%, or 99% or more) of the microbubbles have a radius below that corresponding to a resonance frequency equal to the applied ultrasound frequency (so that the microbubble resonance frequency exceeds the applied ultrasound frequency). This may maximize microbubble response to the applied ultrasound at the target BBB region relative to the microbubble response within the healthy tissue surrounding the target BBB region, as well as tissues along the path between the transducer and the target BBB region. As a result, microbubbles at the non-target region are unresponsive to the relatively low acoustic field to avoid tissue damage, whereas microbubbles at the target region (where the acoustic field is relatively high due to the focused beam) may oscillate and/or collapse, thereby causing tissue disruption effect. Approaches to determining and selecting a desired size distribution of microbubbles are provided, for example, in U.S. Patent Application entitled "Ultrasound Frequency and Microbubble Size Optimization in Microbubble-Enhanced Ultrasound Treatment" filed on even date herewith, the contents of which are incorporated herein by reference.

In step 110, a series of sonications is then computationally applied to the microbubbles at the target BBB region in accordance with the determined ultrasound parameter values. In step 112, the simulation may predict an acoustic response from the microbubbles based on the applied ultrasound parameter values, the geometry of the ultrasound transducer and its position and orientation relative to the microbubbles, the anatomic/material characteristics of the intervening tissue and the characteristics of the microbubbles. For example, the acoustic response may include an acoustic response level representing the temporal acoustic effect of the microbubbles after each sonication pulse and/or an acoustic response dose that represents the cumulative effect of the microbubbles over a single sonication or multiple sonications.

In some embodiments, the treatment-planning simulation computationally predicts creation of additional microbubbles induced by the applied acoustic energy and the injected microbubbles. Therefore, the acoustic response from the microbubbles may be predicted from a combination of the injected microbubbles and microbubbles additionally created in the target BBB region during sonications.

In step 114, the parameter values (e.g., power of energy) of the applied ultrasound waves/pulses and/or the characteristics of the injected microbubbles are computationally adjusted until a microbubble cavitation event occurs at the target BBB region. For example, increasing the acoustic power may generally induce microbubble cavitation. But because increasing the acoustic power may also cause damage to the intervening tissue and/or tissue surrounding the target BBB region, in some embodiments, the acoustic power may have an upper boundary. Once the boundary is reached, the simulation may increase, for example, the microbubble concentration and/or microbubble size (such that the resonance frequency of microbubbles differs less from the ultrasound frequency) in order to cause the cavitation, instead of increasing acoustic power; this avoids undesired damage to the non-target tissue.

In step 116, the tissue disruption effect of the target BBB region and/or non-target regions resulting from microbubble cavitation is computationally predicted based at least in part on the established tissue model of the target BBB region and/or non-target regions. The disruption effect may include the volumetric size of the disrupted BBB region and the estimated degree of disruption, and in one implementation, is captured with a suitable biological parameter (e.g., a vessel size in the target BBB region, the perfusion rate in the target BBB region, an opening size or degree of the target BBB region, the rate at which molecules pass through the BBB region (e.g., the tissue permeability rate, and/or the size of the molecules that are to pass through the BBB region) associated with the target BBB region. In one embodiment, the disruption effect is predicted based on a retrospective study of the patients who have undergone ultrasound-induced cavitation prior to clinical treatment. For example, before clinical treatment, an MRI contrast agent having substantially the same molecular weight (or other size metric) as the therapeutic agent to be injected for tumor treatment may be introduced into the target BBB region after the cavitation event occurs. By monitoring the way that the MRI contrast agent penetrates and diffuses in the target BBB region, it can be determined whether and to what extent the target BBB region has been opened to the therapeutic agent to be injected. The relationship between the cavitation effect and tissue disruption effect may then be established and incorporated into the physical model underlying the simulation. This relationship may empirically improve as the number of patients and/or performed treatments increases. Approaches to empirically establishing the relationship between the microbubble cavitation and tissue disruption effect are provided, for example, in U.S. Patent Application entitled "Cavitation-Enhanced Targeted Drug Delivery and Dosing" filed on even date herewith, the contents of which are incorporated herein by reference. In some embodiments, the treatment-planning simulation also predicts the tissue disruption effect of the non-target regions using similar approaches.

In step 118, the computed tissue disruption effect of the target BBB region and/or non-target regions is then compared against a target objective (such as the desired target value of the biological parameter described above and/or the safety threshold associated with the non-target region). If the computation deviates from the desired target objective by more than a tolerable amount (e.g., 10%), the simulated treatment procedure is adjusted (step 120). The adjustment may be implemented in two approaches. In the first approach, the treatment plan is rolled back, and steps 106-120 are iteratively performed until the simulated tissue disruption effect achieves the target objective. In another approach, the treatment plan is extended to include further sonications—i.e., new settings of the treatment profile parameters (e.g., ultrasound parameters and/or characteristics of additional microbubbles) are introduced to treat the target BBB region; again, the treatment plan may be extended until the simulated tissue disruption effect achieves the target objective (step 122). As a result, the 4D treatment plan allows various treatment profile parameters (e.g., sonication properties and/or the microbubble characteristics) to be dynamically adjusted for efficiently and safely treating the 3D target BBB region as a function of time.

Adjustment of the treatment profile parameters generally involves adjusting the microbubble characteristics and/or the ultrasound transducer parameter settings. In one embodiment, the administration rate, dosage, concentration, and/or timing of the administration of microbubbles is computationally tailored to optimize the treatment efficiency (e.g., transiently disrupting tissue in the target BBB region to the target degree so as to create a therapeutic effect or to allow a therapeutic agent to penetrate therethrough) and/or safety (e.g., limiting damage to the non-target tissue). Generally, the optimal microbubble concentration depends on the desired acoustic power—a higher concentration of microbubbles is typically preferred to permit use of a lower acoustic power to achieve microbubble cavitation. When, for example, the tissue surrounding the target BBB region is sensitive to acoustic energy, low-power sonications are employed to avoid damage to the surrounding tissue. In this case, the microbubble concentration may be increased to ensure that the low-power sonications still induce sufficient cavitation events for disrupting the target BBB tissue. Additionally or alternatively, the size of the microbubbles may be increased in subsequent dose(s) such that the resonance frequency thereof differs less from the selected optimal ultrasound frequency; this may cause more microbubble collapse at the target BBB region.

In some embodiments, a constant microbubble concentration at the target BBB region is desired so that the tissue disruption is steady rather than varying in magnitude over time. The concentration of injected microbubbles in the patient's bloodstream varies over time in accordance with well-understood principles of pharmcokinetics, rising to a peak level following administration and then falling; any administration profile, in other words, results in a predictable concentration profile. Hence, the treatment-planning simulation may generate a steady concentration level by computationally simulating injection of the microbubbles at a constant rate and waiting for them to diffuse and reach a steady state, with continued injection to maintain the steady-state condition. Alternatively, the microbubbles may be computationally injected at a relatively higher rate for initiating the treatment; a relatively lower injection rate may then be used during the course of simulated treatment. In other embodiments, it is desired to increase the microbubble concentration as the treatment proceeds (so as to reduce the sonication power for safety purposes); in this case, the treatment-planning simulation may continuously or discretely increase the microbubble injection rate over time. Regardless of which administration profile is used, when determining the microbubble administration profile, the acoustic power (e.g., temporal acoustic power) and/or acoustic energy (including cumulative power and acoustic effects during the entire sonication procedure) may be taken into account to avoid undesired damage to the target and/or non-target tissues.

Similarly, the treatment-planning simulation may dynamically adjust the acoustic power and/or acoustic energy based on the predicted microbubble concentrations available during the sonication procedure for disrupting the target BBB tissue. This is critical particularly at the beginning and end of microbubble administration when the microbubble concentration is changing (i.e., not at a steady state). In some embodiments, the acoustic power/energy is computationally increased in response to a reduced microbubble concentration. Increasing the acoustic power/energy above a threshold may beneficially cause generation of the microbubbles in the target BBB region, thereby compensating for the reduced microbubble concentration.

In addition, adjustment of the microbubble administration profile, the acoustic power/energy profile, beam shape profile, and/or a combination thereof may facilitate the disruption rate of the target BBB region. In some embodiments, a desired disruption rate of the target BBB region as a function of time is determined based on the anatomic/material characteristics of the target BBB region and/or the non-target regions for optimizing the treatment efficiency and/or safety. During simulation of the ultrasound treatment, the microbubble administration profile and/or the acoustic power/energy profile may be adjusted until the desired disruption rate is achieved and maintained. Controlling the BBB disruption rate is important because, as explained above, an excessive rate can produce a safety hazard, whereas an insufficient rate reduces efficiency and can also compromise safety, since the duration of treatment can itself pose risks to the patient.

In various embodiments, the acoustic power and/or acoustic energy is controlled between lower and upper boundaries to ensure efficient treatment and patient safety. The lower boundary corresponds to a treatment threshold (i.e., the minimum applied energy needed to induce microbubble cavitation and cause tissue disruption of the target BBB region) and the upper boundary corresponds to a safety threshold (i.e., the maximum tolerable energy that does not damage the intervening tissue and/or tissue surrounding the target BBB region). Again, the treatment-planning simulation may dynamically determine these lower and upper boundaries based on the available microbubble concentrations at the target BBB region. Additionally, the sonication profile (e.g., a time interval between different sequences of sonications) may be dynamically adjusted. For example, the time interval between two sequences of sonications may be increased to allow microbubbles to be replenished at the target BBB region before the next sonication sequence.

In various embodiments, it may be desirable to disrupt multiple BBB regions corresponding to a single tumor region or multiple discontiguous tumor regions. In a preferred implementation, the multiple target BBB regions are treated sequentially (e.g., in round-robin fashion) until, for example, the tissue disruption on each region satisfies a corresponding target objective. Accordingly, the treatment planning may simulate the BBB treatment sequentially. In addition, the treatment-planning simulation may take into account the effect resulting from treating one target BBB region when simulating treatment of another target BBB region. For example, when one BBB target is upstream of another, disruption of the upstream target BBB region utilizing microbubble cavitation may reduce the concentration of microbubbles available at the downstream target BBB region, thereby changing the disruption effect thereof. Accordingly, treatment planning may simulate such effects based on the amount of microbubbles required for treating the upstream target BBB region and/or previously acquired image information (such as the locations of the two BBB target regions and their locations in the bloodstream).

Alternatively, the sequential treatment may take another approach, in which the treatment effect on one target BBB region has to satisfy a desired target objective before another target BBB region is simulated. But again, the effect resulting from treatment of the prior target BBB region may be taken into account when simulating treatment of the subsequent target BBB region(s).

In another embodiment, the multiple target BBB regions are treated substantially simultaneously. Steps 106-120 described above are performed to simulate and assess the openings of the target BBB regions. Treatment planning may determine the treatment profile parameters iteratively (beginning with initialized parameter settings), using simulations of the treatment and the predicted effect thereof to adjust the parameters in successive iterations until tissue disruption of each of the target BBB regions satisfies its corresponding target objective.

In some treatment scenarios, the target BBB regions may include multiple types of tissue. The tissues of each type may be grouped together, and the treatment profile parameters, including the transducer parameter settings and/or the microbubble characteristic, may be adjusted to optimally treat each type of tissue (i.e., to achieve its target objectives). Again, different groups of tissue types may be sequentially or substantially simultaneously treated in accordance with the approaches described above.

In an optional step 124, the treatment planning simulation may computationally inject a dose of a therapeutic agent into the target tumor region for treatment. The administration profile of the therapeutic agent may be determined based on retrospective study of patients experiencing the same therapy. Additionally or alternatively, the ultrasound procedure may be performed in combination with other therapeutic methods, such as radiation therapy. For example, after the ultrasound-induced microbubble oscillation/cavitation disrupts vascular tissue in the target region, the radiation therapy may significantly reduce the radiation dose for producing efficient treatment at the target tumor. Again, based on the simulated tissue disruption effect and retrospective study of the patients experiencing the same therapy, the treatment planning simulation may determine the radiation dose for treatment.

Accordingly, treatment planning in the present invention is, generally, an iterative process that may utilize testing of the simulated treatment plan at various stages. The planner may go back to adjust one or more previous treatment profile parameters (e.g., ultrasound settings and/or microbubble characteristics), continue with the next sonication (often determining the subsequent treatment profile parameters from the simulation results of the precedent treatment profile parameters), or even switch the planning to an entirely new target BBB region (e.g., return to step 104, which allows the physician to select a target BBB region for planning).

Once treatment planning for the target BBB region(s) is complete, the treatment plan may be presented to a physician. The physician may modify the plan, e.g., by changing the treatment order of the target BBB regions or indicating a target BBB region for which treatment planning is to be repeated. When the physician finds the treatment plan acceptable, actual treatment may be commenced automatically or manually in accordance with the plan. For example, the ultrasound transducer may be operated based on the settings of the sonication parameters (e.g., amplitudes, phases, directions, and/or time intervals between two series of sonications) determined in the simulation. Thus, while 1 second is a typical sonication suspension time between two consecutive series of sonications, during treatment planning it may be determined that a sonication suspension time of, e.g., 20 seconds is necessary after application of the second series so as to allow the microbubble concentration in the target region to be replenished (i.e., for the microbubbles to be delivered from a syringe to the target BBB region in the brain); this plan may be followed during treatment (i.e., the sonications are suspended for 20 seconds after the second series of sonications).

During actual treatment, the microbubbles may be introduced intravenously or, in some cases, by injection proximate to the target BBB region using an administration system. Configurations of the administration system and one or more filters for selecting a desired size distribution of microbubbles and introducing the microbubbles into the target region may be found in U.S. Patent Application No. 62/597,076, the contents of which are incorporated herein by reference. In addition, other therapeutic methods, such as radiation therapy may be performed in combination with the ultrasound treatment based on the treatment plan. Approaches to combining the ultrasound and radiation therapy are provided, for example, in U.S. patent application Ser. No. 15/637,163, filed on Jun. 29, 2017, the contents of which are incorporated herein by reference.

In some embodiments, the treatment effect (e.g., the size and/or degree of tissue disruption in the target BBB region) is monitored during execution of the treatment plan (e.g., by using the imaging device) on a patient. If discrepancies between the monitored treatment effect and the previously computed treatment effect are discovered, the treatment plan may be modified. Discrepancies may arise, for example, from inaccuracies in certain parameters of the physical model underlying the simulation. Accordingly, in various embodiments, the measurements taken during actual treatment are used as feedback to adjust the parameters (e.g., by fitting the parameters to the measurements). An updated treatment plan may then be created using the adjusted parameters. Adjustments may be made, first, to a parameter, or set of parameters, having a particularly high associated uncertainty (and which will therefore likely need adjustment) and/or which is known to affect the computed treatment effect greatly (i.e., a parameter to which the treatment effect is very sensitive, e.g., because the treatment effect is a higher-order rather than linear function of the parameter). For example, the acoustic absorption coefficient and microbubble size distribution at the target BBB region may be good candidates for parameter adjustments. If re-computation of the treatment effect based on adjustments to the initially selected parameter(s) does not satisfactorily decrease the discrepancy between observed and target values in the course of treatment, additional parameters may be changed. In some embodiments, the model parameters are ranked according to their uncertainties and/or the model's sensitivity thereto, and this ranking facilitates selection of one or more parameters for adjustment during treatment. Approaches to monitoring the treatment effect on the target BBB region and/or non-target regions in real-time during the ultrasound procedure are provided, for example, in U.S. Patent Application No. 62/597,073, filed on Dec. 11, 2017, the contents of which are incorporated herein by reference.

In some embodiments, to the extent that parameters vary as functions of other space- and/or time-dependent quantities (e.g., the tissue type, which generally varies in space, or the temperature, which may change in time), the feedback may inherently encode information about such dependencies, e.g., in the form of spatial or temporal distributions of measured quantities. Parameter adjustment may also be based, at least partially, on human input, e.g., as provided by the physician monitoring treatment. Such human intervention may be assisted by intuitive visual representations of both predictions and measurements (e.g., in the form of boundaries indicating the tissue disruption effect of the target BBB region(s)). The displayed prediction may change dynamically in response to any user manipulation of parameter values. Parameter adjustments may be bounded by pre-set limits to prevent estimated values that are not physically realistic.

In various circumstances, a straightforward adjustment of the existing treatment plan (i.e., an adjustment not requiring complete re-planning) may be carried out, e.g., by propagating the adjustment of the parameter(s) through the model during treatment. For example, if the deviation between the predicted and the measured treatment effect is within a clinically tolerable range, treatment of the currently targeted BBB region may continue, while subsequent planning stages for other target BBB regions may benefit from the feedback.

While measurements of tissue disruption in the target BBB region are described above, the feedback provided during execution of the treatment plan is not limited thereto, but may also include acoustic, thermal or mechanical feedback and/or feedback derived from measurements through analysis and calculations (e.g., of the accumulated thermal dose or cumulative acoustic response dose). For example, the acoustic response emanating from the microbubbles may be detected using a detection device and/or the ultrasound transducer. The detected microbubble response may then be compared against the response predicted by the treatment planning. Approaches to measuring an instantaneous acoustic response level and a cumulative acoustic response dose are provided, for example, in International Application No. PCT/US18/33815, filed on May 22, 2018, the entire disclosure of which is incorporated herein by reference. In addition, approaches to configuring the transducer array for detecting the acoustic signals from the microbubbles are provided, for example, in U.S. Patent Application No. 62/681,282, filed on Jun. 6, 2018, the contents of which are incorporated herein by reference.

Further, feedback received during treatment may include anatomical information and, importantly, information about any changes relative to the patient's anatomy as it existed at the time treatment was planned. Often, significant changes result from unavoidable patient motion during the treatment. Motion-tracking approaches may be employed to detect deformations and positional changes of relevant target or non-target regions, and facilitate adjustments to the treatment plan (e.g., via image-registration approaches) to compensate for such changes. Further, as movements and other changes are generally expected to occur during treatment (within certain limits), they may be taken into account by strategically planning the treatment, e.g., by specifying the order in which various regions are treated in a way that expected changes do not interfere with treatment or substantially increase treatment risk. Approaches to registering images acquired using two or more imaging systems are provided, for example, in U.S. Pat. No. 9,934,570, and approaches to tracking the motion of a treatment target or other objects of interest in an anatomical region of interest in real time during a treatment procedure are provided, for example, in U.S. Patent Publication No. 2017/0358095; the contents of these documents are incorporated herein by reference.

Figure 2A:
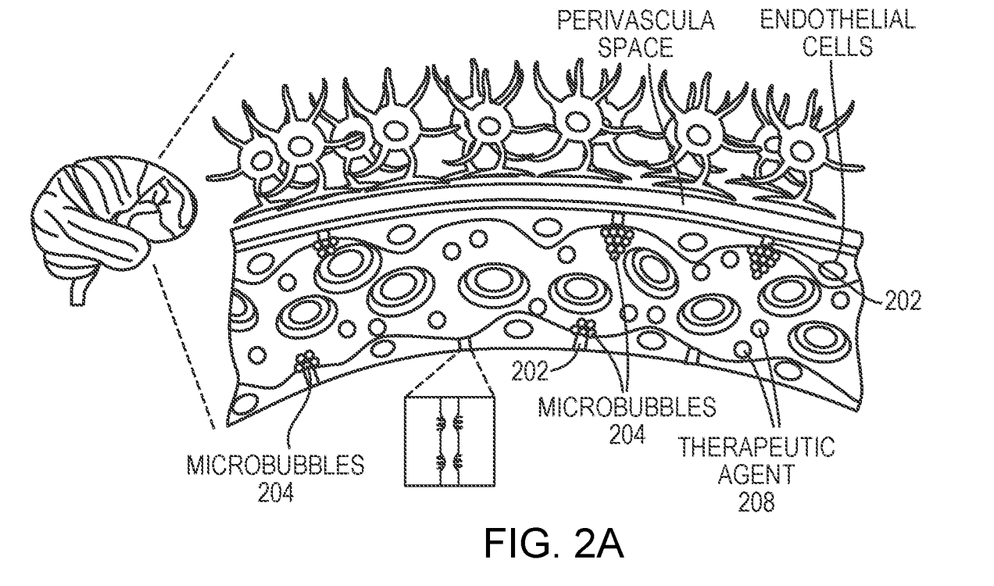
FIG. 2A schematically depicts the BBB excluding a therapeutic agent from reaching a patient's brain tissue.
Figure 2B:
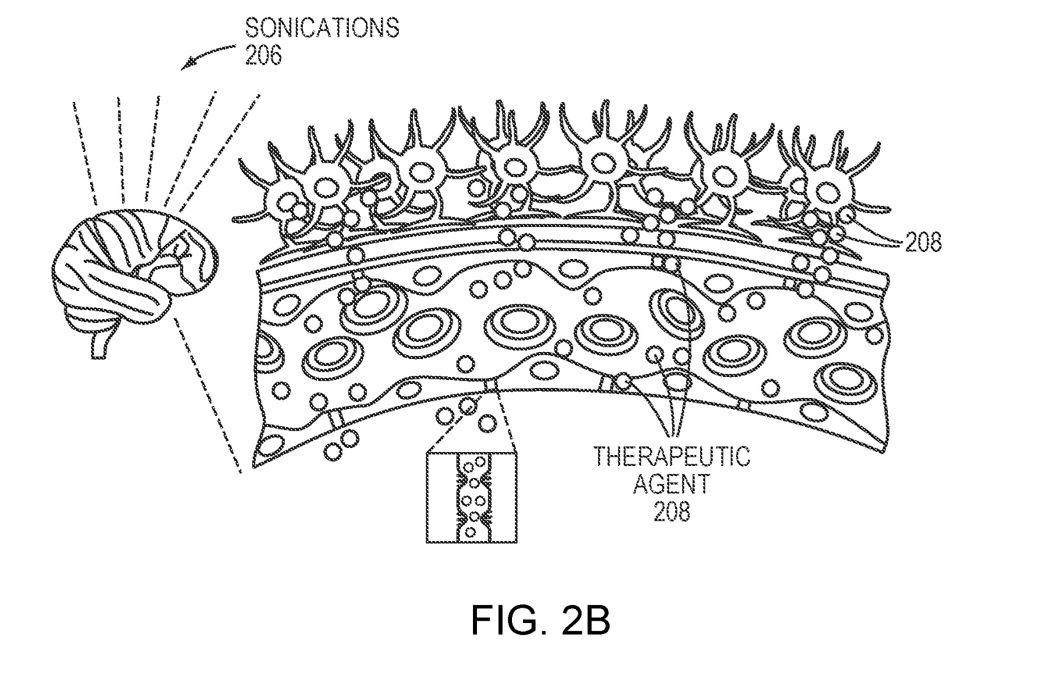
FIG. 2B schematically depicts a microbubble-enhanced ultrasound procedure for temporarily and locally opening the BBB to permit the therapeutic agent to access the brain tissue in accordance with various embodiments.

FIG. 2A schematically depicts how the BBB prevents a therapeutic agent from reaching a patient's brain tissue. In various embodiments, upon acquisition of the images of the patient's brain (in step 102), a treatment planner may communicate with the imaging device to upload the images. As set forth in the flow chart of FIG. 1, the treatment planner may identify one or more target BBB regions 202. Optionally, the planner may computationally inject microbubbles 204 to the target BBB region(s) 202 during treatment simulation. Referring to FIG. 2B, the planner may then computationally apply a series of sonications 206 to the microbubbles at the target BBB region(s). Based on the settings of the treatment profile parameters (e.g., microbubble characteristics and/or ultrasound parameter values) and the anatomic/material properties of intervening tissue located on the beam path between the transducer and the target BBB region, the planner may predict the acoustic response from the microbubbles 204. Subsequently, the planner may predict the degree of tissue disruption in the target BBB regions based on the anatomic/material properties thereof and the predicted microbubble response. If the microbubble-enhancing ultrasound treatment is performed in combination with other therapeutic methods, such as targeted drug delivery, the treatment planner may computationally inject a dose of a therapeutic agent 208 and predict the response. Again, once treatment planning for the target BBB region(s) is complete, the actual treatment may be carried out in accordance with the plan.

Figure 3A:
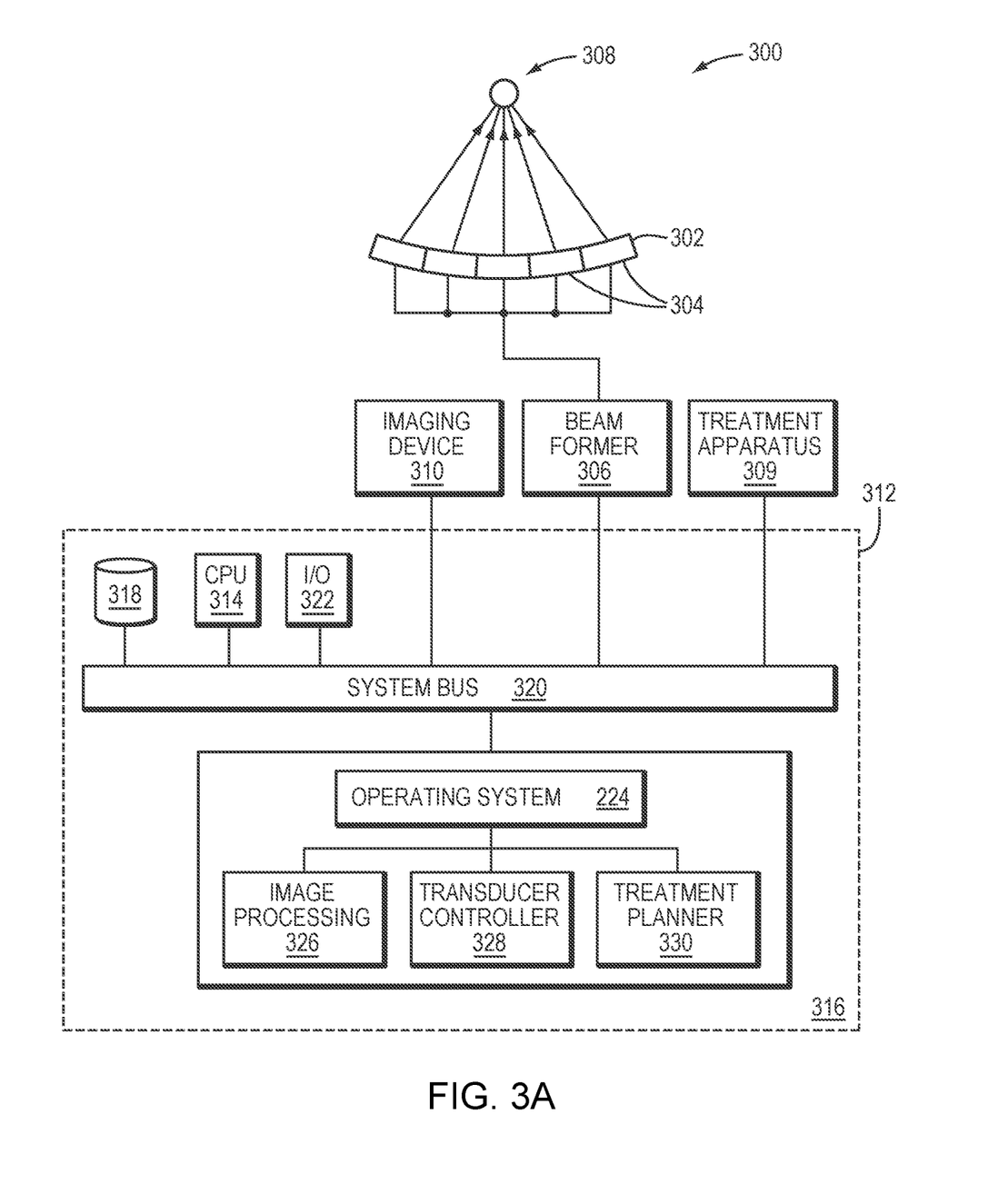
FIGS. 3A and 3B schematically illustrate an exemplary system for planning and executing focused ultrasound treatment in accordance with various embodiments.

FIG. 3A schematically illustrates an exemplary system 300 for planning and executing focused ultrasound treatment as described above. The system 300 includes an ultrasound transducer 302 comprising a one-, two- or three-dimensional arrangement of transducer elements 304, which may, e.g., be piezoelectric ceramic elements or piezo-composite elements. The transducer 302 may be curved (as shown) or planar, and may form a single surface, or include multiple discontiguous and, optionally, independently movable segments. The transducer elements 304 may be individually controllable, i.e., each element may be capable of emitting ultrasound waves at amplitudes and/or phases that are independent of the amplitudes and/or phases of the other transducer elements 304. Alternatively, the elements 304 may be grouped, and each group may be controlled separately.

Collectively, the transducer elements 304 form a "phased array" capable of steering the ultrasound beam in a desired direction, and moving it during a treatment session based on electronic control signals provided by a beam former 306. The beam former 306 typically includes electronic control circuitry including amplifier and phase delay circuits for the transducer elements 304. It may split a radio-frequency (RF) input signal, typically in the range from 0.1 MHz to 10 MHz, to provide a plurality of channels for driving the individual transducer elements 304 (or groups thereof) at the same frequency, but at different amplitudes and phases so that they collectively produce a focused ultrasound beam 308. The system 300 may also include other treatment apparatus 309, such as an administration device for administration a therapeutic agent to the target tumor regions or a radiation device.

The therapeutic agent may include any drug that is suitable for treating a tumor. For example, for treating glioblastoma (GBM), the drug may include or consist of, e.g., one or more of Busulfan, Thiotepa, CCNU (lomustine), BCNU (carmustine), ACNU (nimustine), Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/aldoifosfamide, Bevacizumab, 5-Fluorouracil, Bleomycin, Hydroxyurea, Docetaxel, Cytarabine (cytosine arabinoside, ara-C)/ara-U, etc.

In addition, for treating GBM, those skilled in the art can select a drug and a BBB opening regime optimized to enhance drug absorption across the BBB within patient safety constraints. In this regard, it is known that the BBB is actually already disrupted in the core of many tumors, allowing partial penetration of antitumor drugs; but the BBB is widely intact around the "brain adjacent to tumor" (BAT) region where invasive/escaping GBM cells can be found, and which cause tumor recurrence. Overcoming the BBB for better drug delivery within the tumor core and the BAT can be accomplished using ultrasound as described herein. The drugs employed have various degrees of toxicity and various penetration percentages through the BBB. An ideal drug has high cytotoxicity to the tumor and no BBB penetration (so that its absorption and cytotoxic effects can be confined to regions where the BBB is disrupted), low neurotoxicity (to avoid damage to the nervous system), and tolerable systemic toxicity (e.g., below a threshold) at the prescribed doses. The drug may be administered intravenously or, in some cases, by injection proximate to the tumor region.

In various embodiments, the system 300 further includes an imaging device (e.g., an MRI apparatus or other imaging device) 310 that images (e.g., tomographically) a region of interest in the patient both prior to treatment for the purpose of treatment planning and during treatment for the purpose of guiding the ultrasound beam and monitoring treatment progress. In addition, the system 300 includes a computational facility 312, in communication with the beam former 306 and the imaging device 310, that facilitates treatment planning and adjustment. The computational facility 312 may be implemented in any suitable combination of hardware, software, firmware, or hardwiring; in the illustrated embodiment, it is provided by a suitably programmed general-purpose computer. The computer may include a central processing unit (CPU) 314 and system memory 316, as well as, typically, one or more non-volatile mass storage devices 318 (such as one or more hard disks and/or optical storage units). The computer 312 further includes a bidirectional system bus 320 over which the CPU 314, memory 316, and storage devices 318 communicate with each other and with internal or external input/output devices, such as traditional user interface components 322 (including, e.g., a screen, a keyboard, and a mouse) as well as the beam former 306 and the imaging device 310.

The system memory 316 contains instructions, conceptually illustrated as a group of modules, that control the operation of CPU 314 and its interaction with the other hardware components. An operating system 324 directs the execution of low-level, basic system functions such as memory allocation, file management and operation of mass storage devices 318. At a higher level, one or more service applications provide the computational functionality required for treatment planning and execution. For example, as illustrated, the system may include an image-processing module 326 for displaying, analyzing, and annotating images received from the imaging device 310 and a transducer control module 328 for computing the relative phases and amplitudes of the transducer elements 304.

Figure 3B:
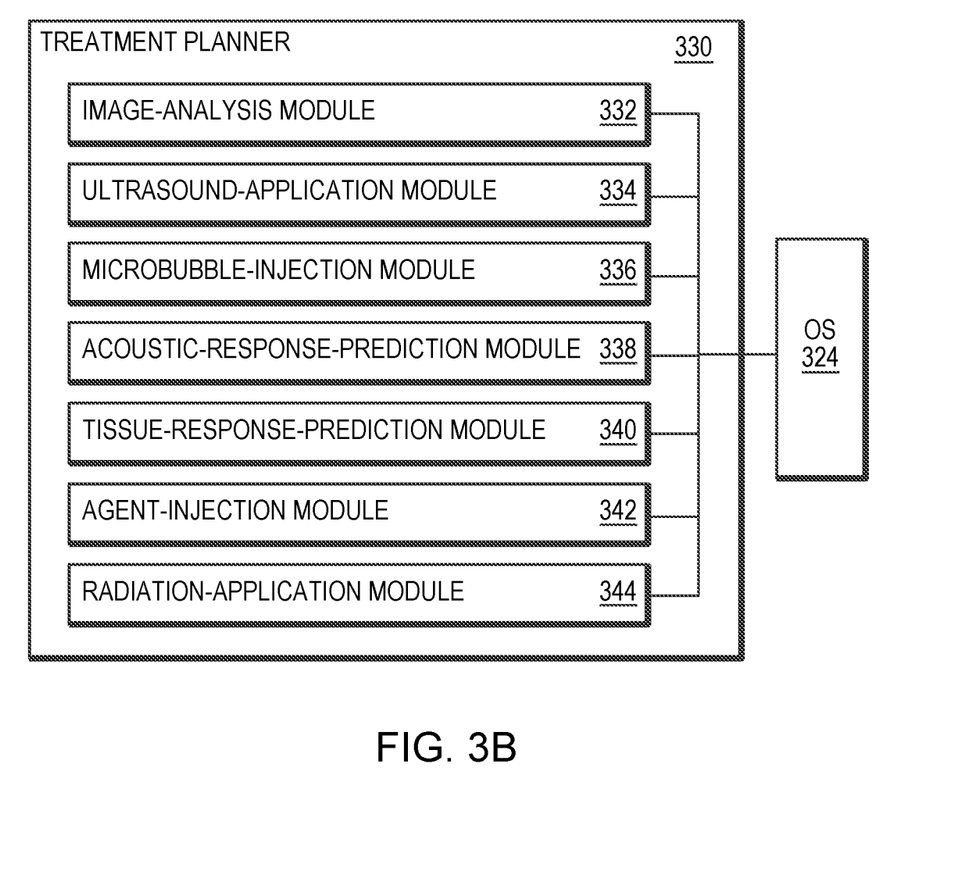

Further, the system includes a treatment planner 330 that determines the sequence, locations, and treatment profile parameters of a series of sonications based on the processed images and user input; the resulting treatment plan may be used by the transducer controller 328 to determine the phase and amplitude settings and/or by the administration device 309 to determine the microbubble administration profile. Referring to FIG. 3B, the treatment planner 330 may, itself, include a number of separate, but intercommunicating modules for performing the simulation steps and functions described above. For example, the treatment planner 330 may include an image-analysis module 332 for processing and analyzing image data received from the imaging device 310 and based thereon determine a target tumor region and/or a target BBB region in the images, an ultrasound-application module 334 for computing the settings of ultrasound parameters for generating a focal zone at the target BBB region, a microbubble-injection module 336 for determining desired microbubble characteristics (e.g., based on retrospective study of the patients experiencing microbubble-enhanced ultrasound procedure and/or using a physical model), an acoustic-response-prediction module 338 for predicting the acoustic response from the microbubbles based on the microbubble characteristics and ultrasound settings, a tissue-response-prediction module 340 for predicting the tissue disruption effect at the target BBB region and/or non-target region based on the predicted microbubble response and/or anatomic/material properties of the target/non-target tissue. In one implementation, the treatment planner 330 further includes an agent-injection module 342 for determining the administration profile of a therapeutic agent for treating the target tumor tissue. Alternatively, the treatment planner 330 may include a radiation-application module 344 for applying a radiation does to the target tumor tissue. The various modules utilize the techniques described above and may be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages; in some embodiments, different modules are programmed in different languages. As will be readily understood by a person of skill in the art, the computational functionality required to carry out treatment-planning methods in accordance herewith may be organized (in software modules or otherwise) in many different ways, and the depicted embodiment in FIGS. 3A and 3B is, therefore, not to be regarded as limiting.

In general, the terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A system for treating a target blood-brain barrier (BBB) region within a tissue region of interest, the system comprising:
   an ultrasound transducer;
   a processor; and
   memory storing (i) a sonication parameter for applying at least one sequence of sonications to the target BBB region using the ultrasound transducer, (ii) a microbubble characteristic for microbubbles selected to be administered into the target BBB region, and (iii) instructions which, when executed by the processor, cause the processor to:
   (a) electronically simulate treatment in accordance with the sonication parameter and the microbubble characteristic at least in part by computationally executing the at least one sequence of sonications and computationally administering the microbubbles having the microbubble characteristic;
   (b) computationally predict a degree of tissue disruption of the target BBB region resulting from the treatment based on the simulation thereof;
   (c) computationally generate a treatment protocol specifying the sonication parameter and the microbubble characteristic based at least in part on the predicted degree of tissue disruption; and
   (d) activate the ultrasound transducer in accordance with the treatment protocol.

2. The system of claim 1, wherein the processor is further configured to predict the degree of tissue disruption as a function of time.

3. The system of claim 1, wherein the sonication parameter comprises an amplitude, a frequency, a beam shape, a phase, or a direction of at least one sonication in the at least one sequence of sonications.

4. The system of claim 1, wherein the processor is further configured to:
   (e) compare the predicted degree of tissue disruption against a target objective; and
   (f) if the predicted degree of tissue disruption deviates from the target objective, alter the treatment protocol and repeat (a) through (d) for the altered treatment protocol, wherein altering the treatment protocol includes altering the microbubble characteristic.

5. The system of claim 4, wherein the target objective comprises at least one of opening of the target BBB region, a target perfusion rate at the target BBB region, a target tissue permeability at the target BBB region, a safety threshold associated with the target BBB region or a safety threshold associated with tissue outside the target BBB region.

6. The system of claim 1, wherein the treatment protocol specifies a plurality of sequences of sonications, and the processor is further configured to:
   (e) compare the predicted degree of tissue disruption against a target objective; and (f) if the predicted degree of tissue disruption deviates from the target objective, alter the microbubble characteristic in a subsequent sequence of sonications.

7. The system of claim 1, wherein the treatment protocol specifies a plurality of sequences of sonications and the sonication parameter is a time interval between consecutive sonication sequences.

8. The system of claim 1, wherein the processor is further configured to obtain a digital image of at least a portion of the target BBB region, and computationally identify a set of 3D voxels corresponding to the portion of the target BBB region and generate the treatment protocol based on the identified 3D voxels.

9. The system of claim 8, wherein a plurality of target BBB regions are identified in the image and the treatment protocol specifies a plurality of sonication sequences each corresponding to one of the plurality of target BBB regions.

10. The system of claim 9, wherein the processor is further configured to substantially simultaneously computationally apply the plurality of sonication sequences to the plurality of target BBB regions.

11. The system of claim 9, wherein the processor is further configured to sequentially computationally apply the plurality of sonication sequences to the plurality of target BBB regions in round-robin fashion.

12. The system of claim 11, wherein the processor is further configured to computationally predict microbubble cavitation resulting from the computationally executed sonications, and predict the degree of tissue disruption of the plurality of target BBB regions based at least in part on the predicted microbubble cavitation.

13. The system of claim 12, wherein the processor is further configured to determine a sonication parameter associated with a second sonication sequence applied to a second target BBB region based at least in part on at least one of (i) the predicted microbubble cavitation or (ii) the degree of tissue disruption resulting from a first sonication sequence previously applied to a first target BBB region.

14. The system of claim 8, wherein the processor is further configured to identify a plurality of tissue types in the target BBB region of the image, wherein the treatment protocol specifies a plurality of sonication sequences each corresponding to one of the identified tissue types.

15. The system of claim 1, wherein the processor is further configured to predict the degree of tissue disruption based on retrospective administrations of magnetic resonance imaging (MRI) contrast agent into target BBB regions of a plurality of patients and diffusion thereof.

16. The system of claim 1, wherein the microbubble characteristic specifies at least one of an agent type, a size, a concentration, a dose, an administration rate or timing, or a location of an injection site.

17. The system of claim 1, further comprising a detection system, wherein the processor is further configured to:

(e) cause the detection system to monitor an actual treatment effect resulting from activation of the ultrasound transducer;

(f) compare the actual treatment effect with the computationally predicted degree of tissue disruption; and (g) upon detection of a discrepancy between the actual treatment effect and the predicted degree of tissue disruption, adjust at least one of the sonication parameter or the microbubble characteristic in the treatment protocol.

18. The system of claim 1, wherein the processor is further configured to cause a therapeutic agent to be administered into the target BBB region.

19. The system of claim 18, wherein the therapeutic agent comprises at least one of Busulfan, Thiotepa, Lomustine, Carmustine, Nimustine, Temozolomide, Methotrexate, Topotecan, Cisplatin, Etoposide, Irinotecan/SN-38, Carboplatin, Doxorubicin, Vinblastine, Vincristine, Procarbazine, Paclitaxel, Fotemustine, Ifosfamide/4-Hydroxyifosfamide/ aldoifosfamide, Bevacizumab, 5-Fluorouracil, Bleomycin, Hydroxyurea, Docetaxel, or Cytarabine/ara-U.

20. The system of claim 1, wherein the processor is further configured to cause a radiation dose to be applied to the tissue region.

* * * * *